(12) United States Patent
Imai

(10) Patent No.: US 7,781,749 B2
(45) Date of Patent: Aug. 24, 2010

(54) BEAM IRRADIATION APPARATUS WITH DEEP ULTRAVIOLET LIGHT EMISSION DEVICE FOR LITHOGRAPHIC PATTERN INSPECTION SYSTEM

(75) Inventor: Shinichi Imai, Tokyo (JP)

(73) Assignee: Advanced Mask Inspection Technology, Inc., Yokohama-shi (JP)

( * ) Notice: Subject to any disclaimer, the term of this patent is extended or adjusted under 35 U.S.C. 154(b) by 138 days.

(21) Appl. No.: 12/187,770

(22) Filed: Aug. 7, 2008

(65) Prior Publication Data

US 2009/0084989 A1 Apr. 2, 2009

(30) Foreign Application Priority Data

Sep. 27, 2007 (JP) ............................. 2007-250589

(51) Int. Cl.
*G01J 1/00* (2006.01)
*G01N 21/00* (2006.01)
*G06K 9/46* (2006.01)

(52) U.S. Cl. ................. 250/503.1; 250/504 R; 250/459.1; 250/461.1; 250/482.1; 250/492.22; 382/190; 382/191; 356/51; 356/237.1; 356/239.3

(58) Field of Classification Search .............. 250/458.1, 250/459.1, 461.1, 482.1, 492.22, 494.1, 495.1, 250/503.1, 504 R; 382/181, 190, 191, 203; 356/51, 237.1–237.6, 239.1, 239.2, 239.3, 356/239.7, 448

See application file for complete search history.

(56) References Cited

U.S. PATENT DOCUMENTS

| 7,495,756 B2 * | 2/2009 | Imai ................... 356/237.1 |
| 7,656,516 B2 * | 2/2010 | Imai ................... 356/237.1 |
| 2005/0196059 A1 * | 9/2005 | Inoue et al. ............ 382/240 |
| 2009/0053029 A1 * | 2/2009 | Yoshino et al. ......... 414/783 |

FOREIGN PATENT DOCUMENTS

| AP | 05-011299 | 1/1993 |
| JP | 02-262389 | 10/1990 |
| JP | 8-76359 | 3/1996 |

OTHER PUBLICATIONS

Japanese Office Action for Application No. 2007-250589, issued May 11, 2010, with English translation - 5 pages.

* cited by examiner

*Primary Examiner*—Bernard E Souw
(74) *Attorney, Agent, or Firm*—Oblon, Spivak, McClelland, Maier & Neustadt, L.L.P.

(57) ABSTRACT

An illumination beam irradiation apparatus for use in pattern inspection systems is disclosed, which is less in deterioration of optical components and in attenuation of illumination light. The illumination apparatus includes a light source which yields a fundamental wave, a beam-shaper unit which performs beam-shaping of the fundamental wave so that this wave has a prespecified shape, and a pattern generator unit which operates, upon receipt of the beam-shaped fundamental wave, to convert this incoming wave into illumination light with a shorter wavelength to thereby generate illumination light of a prespecified shape. The illuminator also includes an image relay unit for guiding the illumination light that was generated by the pattern generator to fall onto a workpiece under inspection, such as a photomask or else.

20 Claims, 7 Drawing Sheets

BEAM IRRADIATION APPARATUS WITH DEEP ULTRAVIOLET LIGHT EMISSION DEVICE FOR LITHOGRAPHIC PATTERN INSPECTION SYSTEM

CROSS-REFERENCE TO RELATED APPLICATION(S)

Priority is claimed to Japanese Patent Application No. 2007-250589, filed Sep. 27, 2007, the disclosure of which is incorporated herein by reference.

TECHNICAL FIELD

The present invention relates generally to semiconductor micro-photolithography technologies and, more particularly, to an illumination apparatus adaptable for use in pattern recognition and inspection of a target object being tested, including a lithographic mask or reticle for use in the manufacture of highly integrated semiconductor devices or liquid crystal display (LCD) panels. This invention also relates to a pattern inspection system using the illumination apparatus.

DESCRIPTION OF RELATED ART

In recent years, the quest for higher integration and larger capacity of ultralarge-scale integrated (ULSI) circuit devices results in noticeable shrinkage of feature size and circuit line width required for semiconductor circuit elements. To fabricate ULSI chips, a repeating pattern of lines and spaces of on-chip circuits is photolithographically transferred onto a silicon wafer by a reduced projection lithography apparatus, called the stepper. In this process, an original or "master" mask plate is used, in which is formed a circuit pattern made up of a great number of highly miniaturized semiconductor circuit elements. This mask is called a photomask or reticle. Obviously, for the manufacture of such mask used to transfer the ultrafine circuit pattern onto wafers, a need is felt to use an advanced photolithography tool capable of drawing or "writing" ultrafine circuit patterns. In some cases, this lithography tool is used to write such patterns on wafers directly. Examples of it are an electron beam (EB) lithography tool and a laser beam lithography tool, which are under almost endless development for achievement of higher performances.

For costly fabrication of ULSI chips, it is inevitable to improve manufacturing yields. Unfortunately, it is likely that such yield improvement fails to catch up rapid growth in microfabrication of ULSI chips, the minimum feature size of which is becoming smaller to shift from the sub-micron order to nanometer orders, as in one-gigabit (1 GB) dynamic random-access memory (DRAM) devices. One major factor that lowers the yield must be the presence of pattern defects of a photomask that is used for lithographic transferring of an ultrafine circuit pattern onto semiconductor wafers. Recent advances in miniaturization of ULSI chip patterns to be formed on silicon wafers result in likewise decreases in minimal detectable size dimensions of pattern defects. This in turn requires pattern inspection apparatus for checking a pattern transfer mask for defects to further increase in defect detection accuracy.

Recent advances in multimedia technology for personal computers (PCs) require LCD panels to increase in size of built-in drive circuit substrate up to 500 mm by 600 mm or greater and, at the same time, to decrease in minimum linewidth of a pattern of electrical circuitry made up of thin-film transistors (TFTs) formed on LCD substrate. This in turn requires pattern inspection apparatus to offer its enhanced testing ability to check large-size LCD panel substrate for ultra-small pattern defects. Thus, it becomes necessary to develop a workpiece inspection tool capable of efficiently checking large-area LCD photomask for defects in a short period of time at increased through-puts.

One prior known pattern inspection apparatus is disclosed, for example, in Published Unexamined Japanese Patent Application (PUJPA) No. 8-76359. The inspection tool as taught thereby includes a magnifying optical system for sensing the circuit pattern formed on a workpiece, such as a lithography mask or else, to thereby obtain its optical pattern image at a given level of magnification. Pattern inspection is then performed by comparing this pattern image to a reference image that was prepared based on the original circuit design data or, alternatively, to another optical image obtained through image capturing of an identical pattern on the workpiece.

Typically the pattern inspection methodology includes a method using the so-called die-to-die (DD) comparison technique and a method using the die-to-database (DB) comparison scheme. The DD comparison is to compare together optical pattern images of the same mask at different locations thereon. The DB comparison method includes the steps of storing computer-aided design (CAD) data of an integrated circuit pattern, inputting this CAD data to a lithographic tool when such CAD design pattern is written on a photomask after having converted the data so as to have a data format adequate for input to this tool, using the CAD data to create a reference image, capturing an optical image of the actually written and measured pattern of the mask, and comparing this measured image to the reference image.

In the inspection process using any one of the DD and DB comparison techniques, the photomask to be tested is placed on a stage structure within the inspection tool. This stage is motor-driven to move in such a way as to permit a beam spot on the mask to scan its pattern area for execution of the inspection. More specifically, a light source and illumination optical system are used to emit a beam of illumination light and then guide it to fall onto the workpiece being tested. Those light rays that passed through the workpiece or light rays that were reflected off therefrom are focused on a photosensor. An optical image picked up by this sensor is photoelectrically converted into its corresponding electrical image signal, which is supplied to a comparator circuit. This comparator compares the optical image to the reference image in accordance with an appropriate algorithm after having performed position alignment therebetween. If the former fails to match the latter, the pattern under inspection is determined to be defective.

As lithography mask patterns decrease in minimum line width and increase in integration density with advances in performances of ULSI chips, pattern inspection apparatus is required to offer higher resolutions. To achieve higher resolutions, it is a must to shorten the wavelength of illumination light. One approach to doing this is to use a laser light source which emits a beam of deep ultraviolet (UV) light as the illumination light for pattern inspection. According to the semiconductor roadmap, illumination light having an inspection wavelength of less than or equal to 266 nanometers (nm) is needed for pattern inspection of ULSI chips of the 90-nm node generation or later generations.

In the case of such laser light or coherent light with a wavelength of 266 nm or less being used as the illumination light, it is inevitable to design illumination apparatus to have extra optical components for beam transmission and beam shaping. If the optical components are situated at locations with high electrical fields being applied thereto, these components can become impaired in quality and function due to the presence of such high electric fields. This deterioration risk is a serious bar to achievement of stable irradiation of the deep UV illumination light.

For adequate illumination control during pattern inspection, it is needed to adjust or "reshape" the shape of an illumination light beam on a case-by-case basis. To do this, a mirror or lens module is often employed. In view of the fact that the illumination light decreases in transmissivity and reflectivity in shorter-wavelength region thereof, deterioration of optical components serves to accelerate degradation of optical characteristics of the illumination light. Accordingly, advantages of the illumination tool design for making the illumination light wavelength shorter than ever before do not come without accompanying problems: the deep UV illumination light is inherently less in use efficiency; and, this efficiency can be further lowered with time due to the deterioration risk of the additionally provided optical components for beam shaping and transferring.

SUMMARY OF THE INVENTION

It is therefor an object of the present invention to provide an illumination apparatus which is less in degradation of optical components thereof. Another object of this invention is to provide an illumination apparatus less in attenuation of illumination light. A further object of the invention is to provide a pattern inspection apparatus of the type having inspection wavelength of 266 nanometers (nm) or less and being less both in degradation of optical components and in attenuation of illumination light.

An illumination apparatus incorporating the principles of this invention is arranged to include a light source for yielding a fundamental wave, a beam-shaping unit for performing beam-shaping of the fundamental wave to thereby cause it to have a prespecified shape, a pattern generator unit responsive to receipt of the beam-shaped fundamental wave for converting it into illumination light with a shorter wavelength and for generating illumination light having a predetermined shape, and an image relay unit for receiving the illumination light generated at the pattern generator unit and for guiding it to fall onto a target object, such as an object under inspection.

In accordance with another aspect of the invention, a pattern inspection apparatus is provided, which includes a light source for emitting a fundamental wave, a beam shaper unit for performing beam-shaping of the fundamental wave in such a way that this wave has a prespecified shape, a pattern generator unit responsive to receipt of the beam-shaped fundamental wave for converting this wave into illumination light with its wavelength of 266 nanometers (nm) or less to thereby generate illumination light having a predetermined shape, an image relay unit for guiding the illumination light generated by the pattern generator unit to hit an aimed object, such as an object being tested, and a light-receiving unit for receiving a pattern of the object.

Major advantages of this invention are as follows. First, according to the illumination apparatus embodying the invention, it is possible to lessen degradation and deterioration of optical components used therein. Second, it is possible for the illumination apparatus to lessen or minimize unwanted attenuation of the illumination light generated. Third, according to the pattern inspection apparatus also embodying the invention, it is possible to suppress deterioration of optical components while at the same time lessening attenuation of illumination light emitted.

BRIEF DESCRIPTION OF THE DRAWINGS

FIG. 1A is a block diagram of an illumination apparatus in accordance with one preferred embodiment of this invention whereas FIG. 1B is a block diagram of one comparative example thereof.

DETAILED DESCRIPTION OF THE INVENTION

Illumination Apparatus

Figure 1:
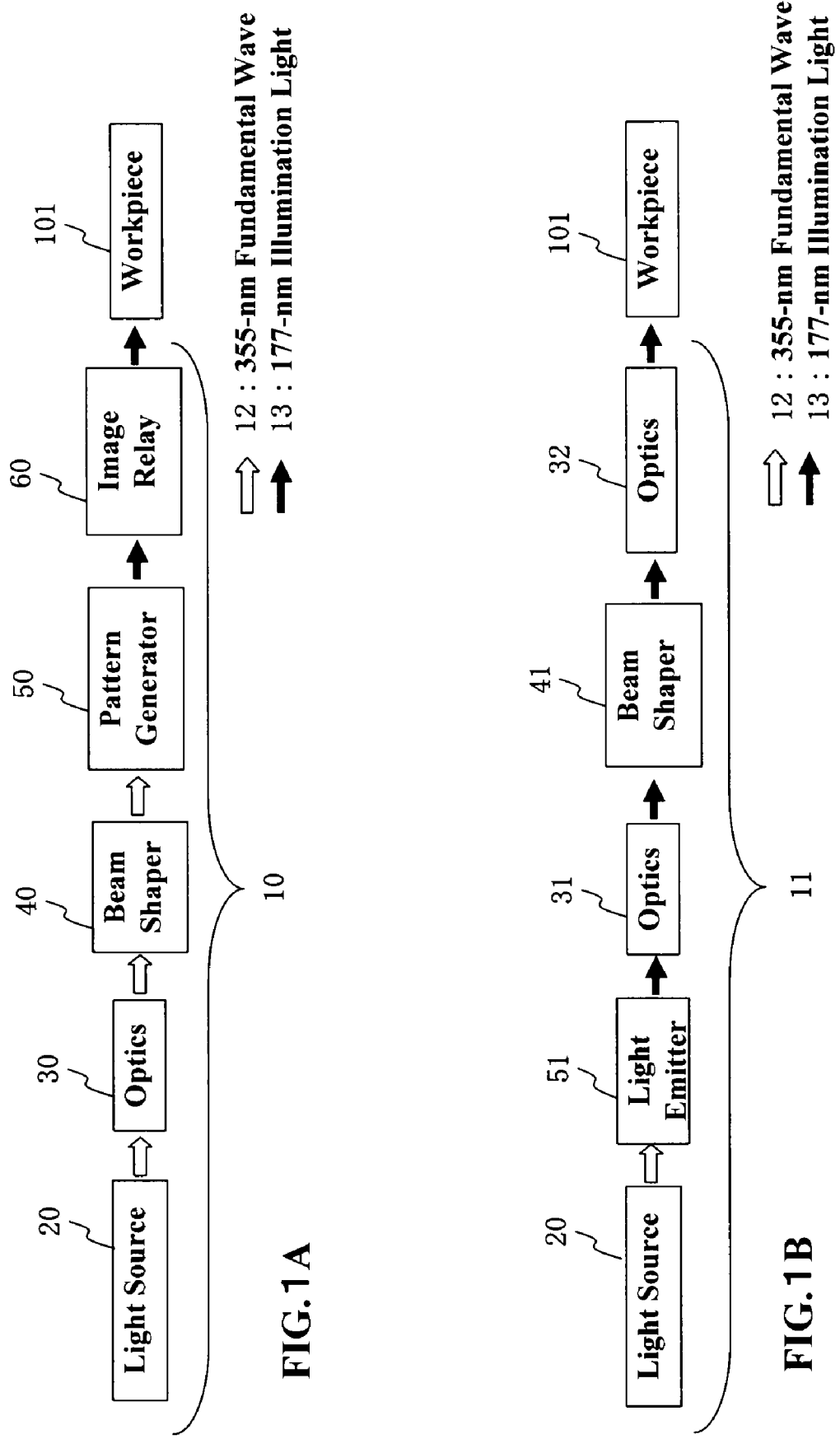

An illumination beam irradiation apparatus in accordance with one preferred embodiment of this invention is shown in FIG. 1A in block diagram form. In FIG. 1A, the illumination apparatus is designated by reference numeral 10. This illumination apparatus 10 is generally made up of a light source 20, optical system 30, beam-shaping unit 40, optical pattern generation unit 50, and image relay unit 60. The light source 20 is for yielding a fundamental wave 12 with a wavelength of 355 nm as an example. The fundamental wave 12 emitted from light source 20 is transferred via the optics 30 to the beam shaper unit 40. This beam shaper is the one that performs beam-shaping of the fundamental wave 12 in a way such that this wave has a specific shape, such as a rectangle or square or else, resulting in production of the beam-shaped fundamental wave 12 having the specific shape. When this specifically shaped fundamental wave 12 enters the pattern generator 50, this unit emits illumination light of shorter wavelength, e.g., deep ultraviolet (UV) light 13 with a wavelength of about 177 nanometers (nm), or more or less. Thus, an optical pattern of the specific shape is generated by pattern generator 50. The deep UV light 13 is sent forth by image relay unit 60 so that UV light 13 falls onto a target object 101, such as a workpiece under pattern inspection.

With the illumination apparatus 10 embodying the invention, pattern generator 50 emits deep UV illumination light 13, which is guided to fall onto target object 101 via a decreased number of optical devices or components which constitute image relay 60. Regarding the waveform of illumination light 13, it is needed to employ a laser light source having an inspection waveform of deep UV range in order to achieve a higher level of resolution. According to recent semiconductor roadmap, it is required to use a pattern inspection beam with its wavelength of 266 nm or less for ultralarge-scale integrated (ULSI) circuit devices of the 90-nm node generation or later generations.

FIG. 1B shows an illumination apparatus 11, which is a comparative example of the illumination apparatus 10 of FIG.

1A. Illumination apparatus 11 includes, for example, a light source 20 which yields a fundamental wave 12 with a wavelength of 355 nm, and a light emitting unit 51 which produces deep UV illumination light 13 having a wavelength shorter than that of the fundamental wave 12 generated from the light source 20. The wavelength of deep UV light 13 is 266 nm or less-preferably, 177 nm. Illuminator 11 further includes an optics 31 for transmission of illumination light 13, a beam-shaper unit 41 for performing beam-shaping so that illumination light 13 has a specific shape such as a rectangle or else, and an additional optics 32 which transfers the beam-shaped illumination light 13 from beam-shaper 41 to a target object 101 to thereby illuminate this object 101. With illuminator 11 of comparative example, deep UV illumination light 13 is directly produced by light emitter 51 and is then irradiated onto object 101 by way of an increased number of optical devices, including the two separate optics 31 and 32 for light transmission and the beam-shaper 41 for beam-shaping processing.

In case the deep UV light of shorter wavelength passes through an optical device, such as a lens module or mirror, when this light is reflected therefrom, its intensity decreases, resulting in the loss of a light amount. In addition, the optical device, such as a lens or mirror, can deteriorate, which leads to occurrence of with-time change in characteristics, also known as the aged deterioration. In brief, the illumination apparatus 11 of comparative example suffers from risks of the loss of illumination light amount and the optical device deterioration due to the fact that an increased number of optical devices are present along the optical path of the deep UV light. In contrast, the illuminator apparatus 10 of this embodiment is capable of suppressing such light amount loss and optical device deterioration. This can be said because the optical devices in the deep UV light path is decreased in number.

Light Source

The light source 20 is a device which yields a fundamental wave 12. Preferably, the fundamental wave 12 is a specific kind of light that is excellent in ability to convert fundamental wave 12 into illumination light required. A typical example of light source 20 is a neodymium (Nd)-doped yttrium-aluminum-garnet (YAG) laser which emits third harmonic wave light with a wavelength of about 355 nm, also known as the third harmonic generation (THG) Nd:YAG laser. In the embodiment apparatus 10, a 355-nm THG Nd:YAG laser named "SL188AT Oscillator" with a repetition frequency of 10 kHz and maximum output power of 50 W was employed. This laser oscillator is commercially available from Laserfront Technologies (LFT) Inc. In the light source of this embodiment, the laser is designed to operate in a Q-switched pulse mode under conditions which follow: pulse repetition frequency was set to 8 kHz; output energy was set at 6 mJ; pulse width, 100 ns; and average output, 48 W.

Figure 2:
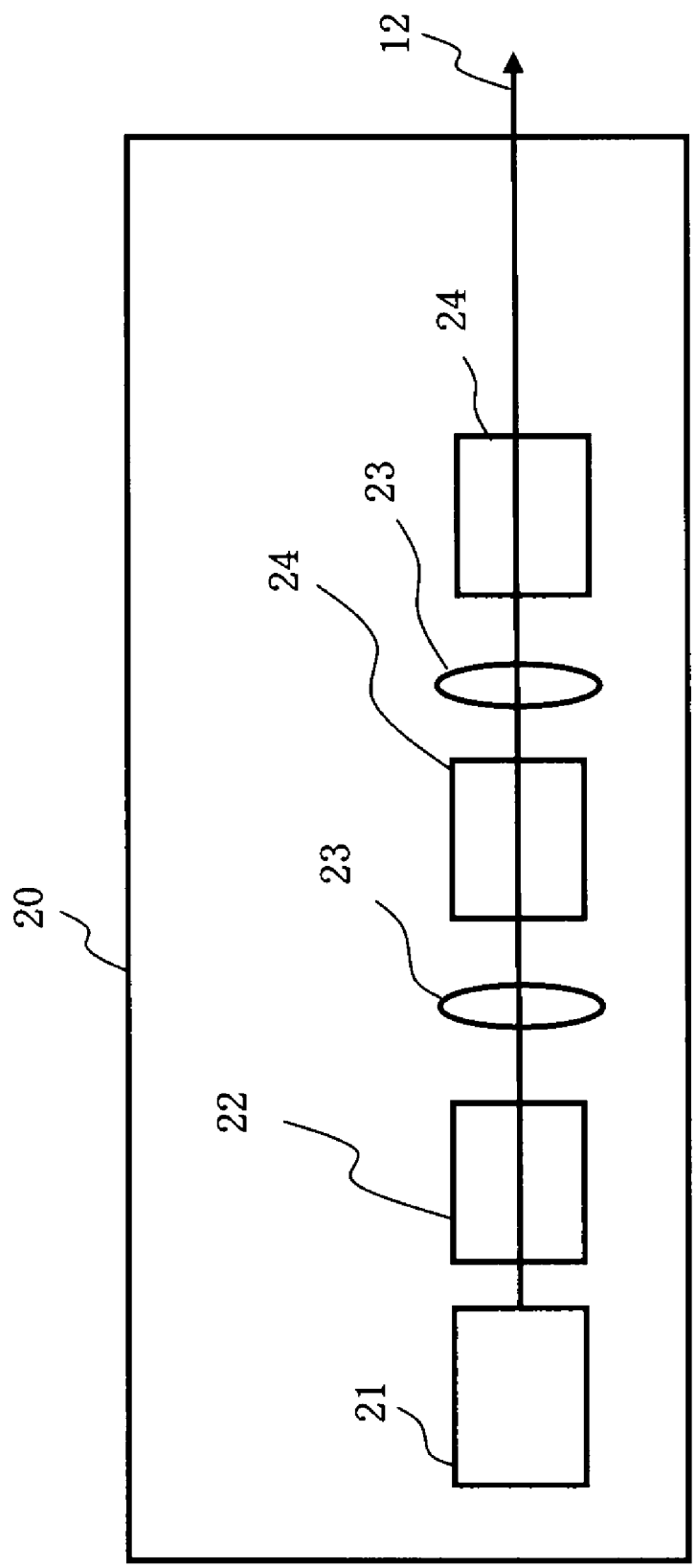
FIG. 2 is a diagram schematically showing an internal configuration of a light source used in the illumination apparatus shown in FIG. 1A.

An internal configuration of the light source 20 is shown in FIG. 2, for explanation of production of the fundamental wave 12. Light source 20 includes a laser oscillator 21, which is constituted from the above-noted 355-nm THG Nd:YAG laser, and a Q-switch modulator which produces pulsed laser light with a wavelength of 1,064 nm. This output laser light is amplified by a Nd:YAG laser amplifier 22 up to an increased power level of 100 W. The output light is for use as the fundamental wave, which is then introduced via a collecting lens or "condenser" 23 into a second harmonic wave generator unit 24, resulting in production of a second harmonic wave with a wavelength of 532 nm. This second harmonic wave and non-converted fundamental wave components are introduced via condenser lens 23 into a third harmonic wave generator unit 24, which produces a wave with its frequency being equal to the sum of frequencies of these two waves, resulting in production of the intended third harmonic wave of the wavelength of 355 nm. This finally obtained wave becomes the fundamental wave 12 of light source 20.

Respective adjacent ones of the above-noted optical devices are optically coupled together by an exclusive-use component. When the need arises, the illustrative optical path of laser light emitted may be modified by using appropriate optics on a case-by-case basis.

Figure 3:
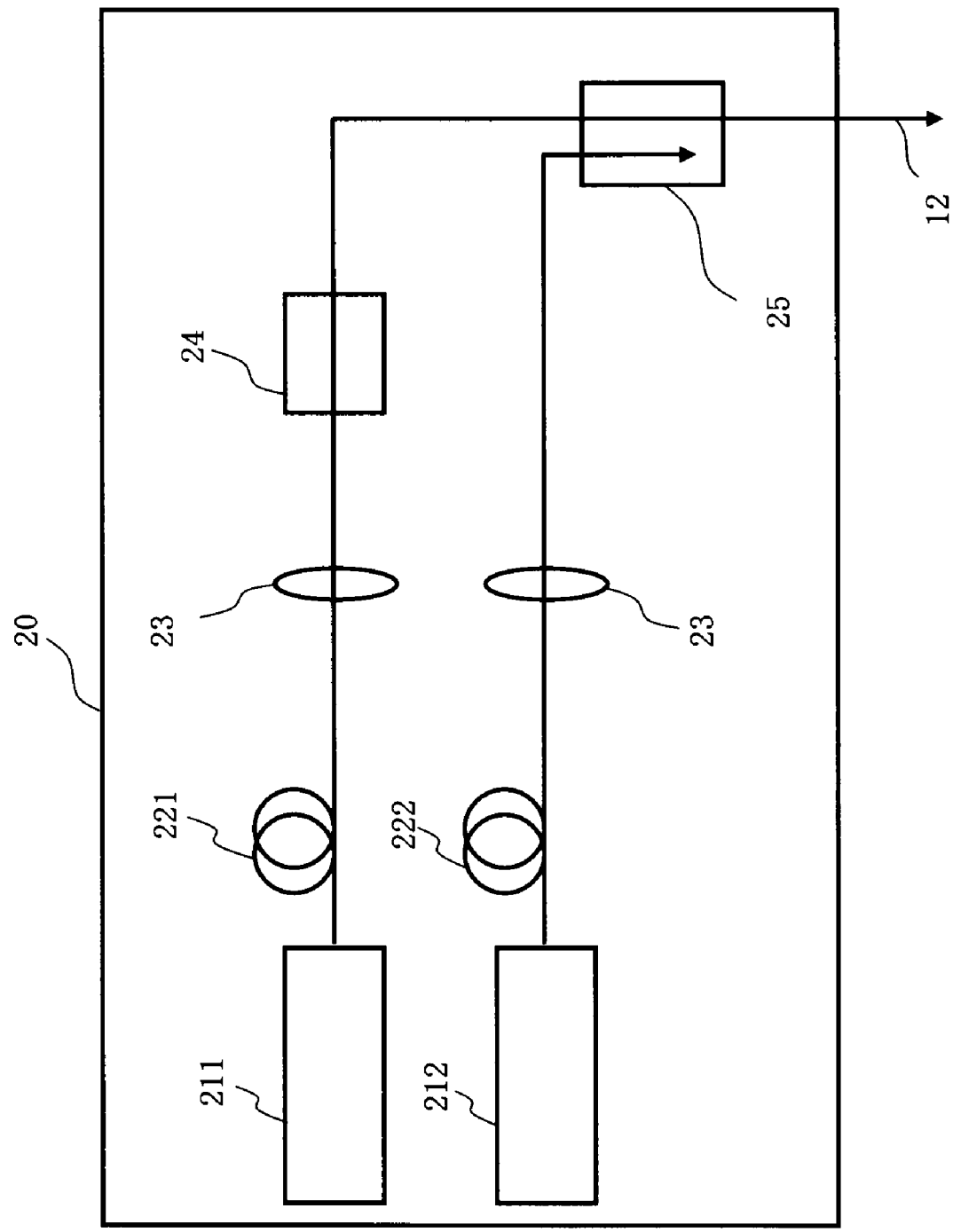
FIG. 3 illustrates a configuration of another light source employable in the illumination apparatus of FIG. 1A.

Another light source 20 which is also employable in the illumination apparatus 10 is shown in FIG. 3 for explanation of an internal configuration thereof. This light source 20 is arranged to include a couple of laser oscillators 211 and 212 for emitting light rays that are different in wavelength from each other. The "first" laser oscillator 211 is for yielding a fundamental wave with first wavelength whereas the "second" laser oscillator 212 is to emit a fundamental wave of second wavelength. The fundamental wave as output from first laser oscillator 211 is designed to travel through an optical fiber 221 and a condenser lens 23 to enter a high harmonic wave generator 24 for conversion to a high-frequency wave. The fundamental wave leaving from second laser oscillator 212 is sent forth via an optic fiber 222 and condenser lens 23. These fundamental waves—i.e., the frequency-converted fundamental wave from first laser oscillator 211 and the "native" fundamental wave from second laser oscillator 212—are then guided to input a sum frequency wave generator 25 in a coaxial manner. Upon coaxial radiation of these incoming waves, the sum frequency wave generator 25 produces a wave with its frequency equal to the sum of frequencies of such input waves. Sum frequency wave generator 25 may typically be constituted from a non-linear crystal body or else.

Beam-Shaper

The beam-shaping unit 40 shown in FIG. 1A is the one that shapes the fundamental wave 12 as transferred via the optics 30, that is, performs beam-shaping. For example, beam-shaper 40 is capable of changing the cross-sectional shape or "profile" of the incoming wave into a variety of kinds of shapes, such as a rectangle or else, in a way conformity with an irradiation portion of target object 101 or, alternatively, uniformizing an intensity distribution within the shape.

Pattern Generator

The optical pattern generator 50 shown in FIG. 1A is the one that receives the beam-shaped fundamental wave 12 for applying thereto wavelength conversion to thereby produce illumination light 13 which is shorter in wavelength than the incoming wave. This wavelength-converted illumination light 13 produced by pattern generator 50 has a prespecified pattern indicative of the optical pattern of the incoming fundamental wave 12. The pattern of illumination light 13 is typically identical to the pattern of fundamental wave 12 although the former may be deformed in shape, partly lacked or changed in size dimensions.

Figure 4:
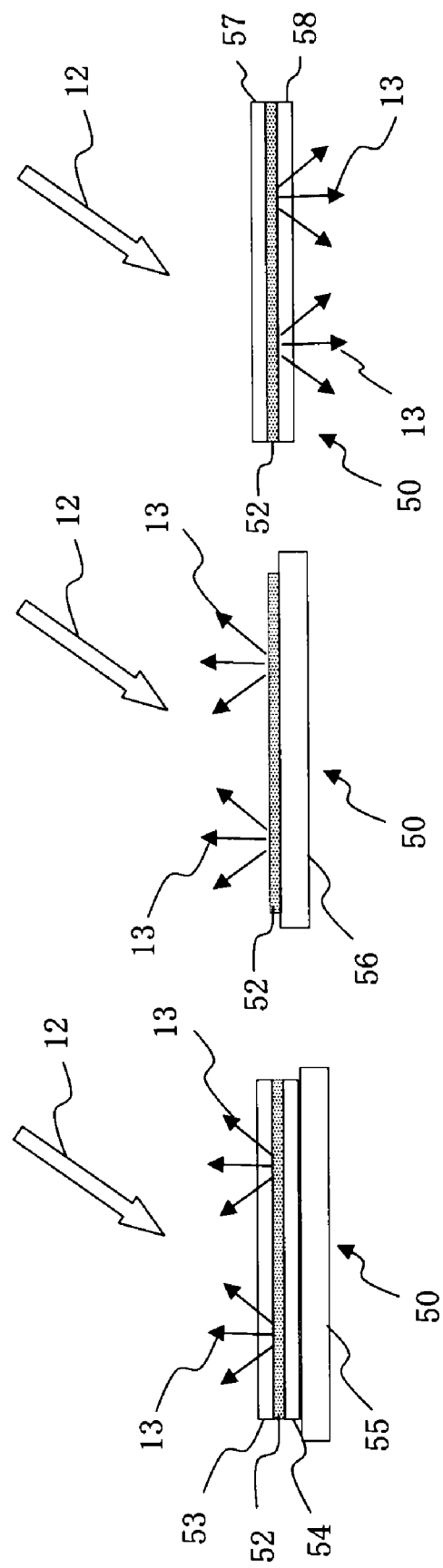
FIGS. 4A to 4C are diagrams for explanation of a pattern generator unit in the embodiment apparatus.

Some examples of the pattern generator unit 50 are shown in FIGS. 4A to 4C. One exemplary pattern generator 50 shown in FIG. 4A is arranged to have a fine-particle nonlinear crystal layer 52 which is interposed between a pair of spaced-apart upper and lower optical transparent plates 53 and 54 made of quartz glass. These glass plates 53-54 are placed on a heat release plate 55, also called the heat sink. The nonlinear crystal layer 52 is made of fine particles or powder of a cesium triborate ($CsB_3O_5$) crystal. The $CsB_3O_5$ or "CBO" particles are typically designed to have a diameter of 100 micrometers (μm) or less—preferably, ranging from 10 μm to 0.1 μm—although the optimum average particle diameter may be variable in value depending upon the kind of the crystal used. This pattern generator 50 has a surface for incoming radiation of the fundamental wave 12 and a surface for output of the illumination light 13, wherein these input and output surfaces are set to the same plane. Use of the powdery CBO crystal enables production of coherent light with a wavelength of 177 nm upon incidence of coherent light of 355-nm wavelength. The upper glass plate 53 is made of quartz having its opposite surfaces that are applied anti-reflective (AR) coating at 355 nm and 177 nm, respectively. The lower quartz glass plate 54 is 355-nm AR-coated on the both surfaces thereof.

Another exemplary structure of the pattern generator 50 is shown in FIG. 4B. This structure has a nonlinear crystal powder layer 52 formed on a substrate 56, which layer is made of CBO crystal particles. This pattern generator is simpler in structure than that shown in FIG. 4A and is similar thereto in that an entrance plane of the fundamental wave 12 and output plane of the illumination light 13 are the same.

A further example of the pattern generator 50 is shown in FIG. 4C. This is made up of a couple of upper and lower quartz glass plates 57 and 58 and a nonlinear crystal powder layer 52 being sandwiched therebetween. This pattern generator has an entrance plane of the incoming fundamental wave 12 and an output plane of illumination light 13, wherein these planes are on the opposite sides of the nonlinear crystal "sandwich" structure. Obviously, the pattern generator 50 should not be construed as being limited only to the light emission structures shown in FIGS. 4A-4C. Pattern generator 50 may be designed to use particle activation-obtainable second harmonic generation (SHG) or, alternatively, use a technique for generating the sum frequency of two or more frequencies. Examples of such other usable pattern generator structures include, but not limited to, a structure using a powdered nonlinear polycrystalline material designed in the form of any one of those shown in FIGS. 4A-4C, and a porous structure for use as a powder method workpiece, which is obtained by pure water treatment of the surface(s) of a nonlinear single-crystalline or polycrystalline material to thereby permit the workpiece to have a substantially increased surface area.

Examples of the nonlinear crystal used for wavelength conversion at a halfway place along the light path are potassium titanate phosphate ($KTiOPO_4$ or "KTP") and beta-barium borate ($\beta$-$BaB_2O_4$ or "BBO"). Note here that regarding the crystals used for the conversion of respective wavelengths, any available crystals are employable as far as these have transparency against the wavelengths concerned and also offer phase matchability in the process of each wavelength conversion.

The pattern generator unit 50 is also capable of producing laser light with a frequency equivalent to the sum of frequencies of more than two incident fundamental waves 12 which enter thereto in a coaxial manner. Typical example of the nonlinear crystal used therefor are lithium triborate ($LiB_3O_5$ or "LBO") and cesium lithium borate ($CsLiB_6O_{10}$ or "CLBO") or like materials.

Figure 5:
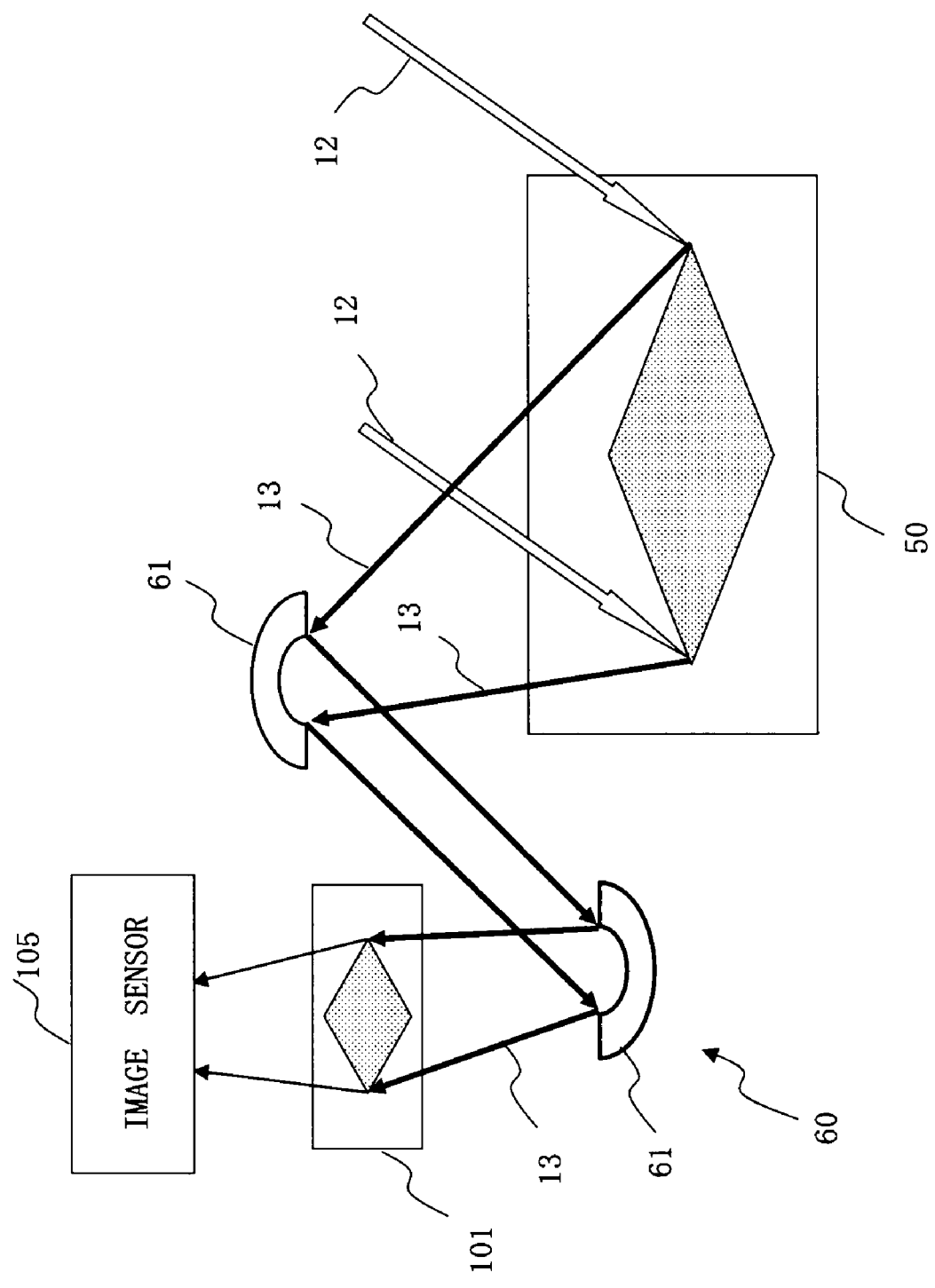
FIG. 5 is a diagram for explanation of the pattern generator and an image relay unit in the embodiment apparatus.

See FIG. 5, which schematically shows an optical system including the pattern generator unit 50 and its associated image relay unit 60. When the beam-shaper unit 40 emits the beam-shaped fundamental wave 12 having a prespecified pattern image, this wave 12 is uniformly irradiated onto a plate-like SHG body surface of the pattern generator 50, resulting in production of illumination light 13 having a prespecified pattern. In this example, the irradiation pattern of fundamental wave 12 is a rectangle with a long side length of 40 mm and a short side length of 10 mm. This becomes irradiation of fundamental wave 12 at an irradiation peak power density of 15 kilowatts per square centimeter (kW/$cm^2$). The conversion efficiency obtainable at this time is 0.2 percent (%), or more or less. Thus, light emission of 96 milliwatts (mW) is obtainable for the shape of 10 mm by 40 mm.

Optical Image Relay

Basically the image relay unit 60 is the one that transmits an optical image at one end to the other; in other words, image relay 60 transfers incident light while retaining the shape thereof. In this embodiment, image relay 60 sends forth the illumination light 13 with the prespecified pattern as output from the pattern generator 50 for causing this light to fall onto the target object 101 under inspection. Note here that the prespecified pattern as output from pattern generator 50 is not necessarily identical to the prespecified pattern irradiated onto object 101 and may alternatively be deformed, partly lack or change in size.

The 177-nm wavelength light that was produced by the pattern generator unit 50 is image-relayed up to the target object 101 in a nitrogen ($N_2$) gas-purged atmosphere. The simplest optical system is an image relay using a couple of concave mirror plates 61. An example of such concave mirror is a dichroic mirror which allows reflection of only light rays with the wavelength of 177 nm. Use of dichroic mirrors for mirrors 61 makes it possible to achieve single-wavelength illumination. With this technique, it was enabled to provide the intended beam-shaping with increased beam handleability in an optical system based on 355-nm wavelength laser light, which is less in risk of deterioration than the 177-nm light and which is greater in commercial availability owing to its nature as to longer wavelength.

As apparent from the foregoing, use of this 355-nm light-based beam shaping makes it possible to determine the shape of 177-nm illumination light. By controlling this shape, the beam shaping scheme becomes employable in a wide variety of off-axis illumination (AOI) applications. The target object 101 being illuminated by such AOI light is subjected to image capturing or "photographing" by the image sensor unit 105 with sensitivity at 177-nm wavelength, followed by a process of determining whether the object is proper or defective, thus enabling execution of the pattern inspection required. Although in the above-noted example the illumination light 13 is designed to be 355-nm coherent SHG light, this may be replaced by a beam of light with its wave frequency equal to the sum of frequencies of two separate coherent light beams, known as the sum frequency generation (SFG) in the art to which the invention pertains.

The above-stated illumination apparatus embodying the invention is capable of using as the illumination light a beam of deep UV light, which has traditionally been unobtainable due to the presence of limits of optics in the prior art, and is also able to use the light source with increased beam shapability and enhanced spectrum controllability. In addition, for performing off-axis illumination (AOI) in deep UV range, it is possible to improve through-puts of the illumination light that is significantly limited by the commercial availability and performances of parts or components used for emission of the light required.

Lithography Pattern Inspection System

Figure 6:
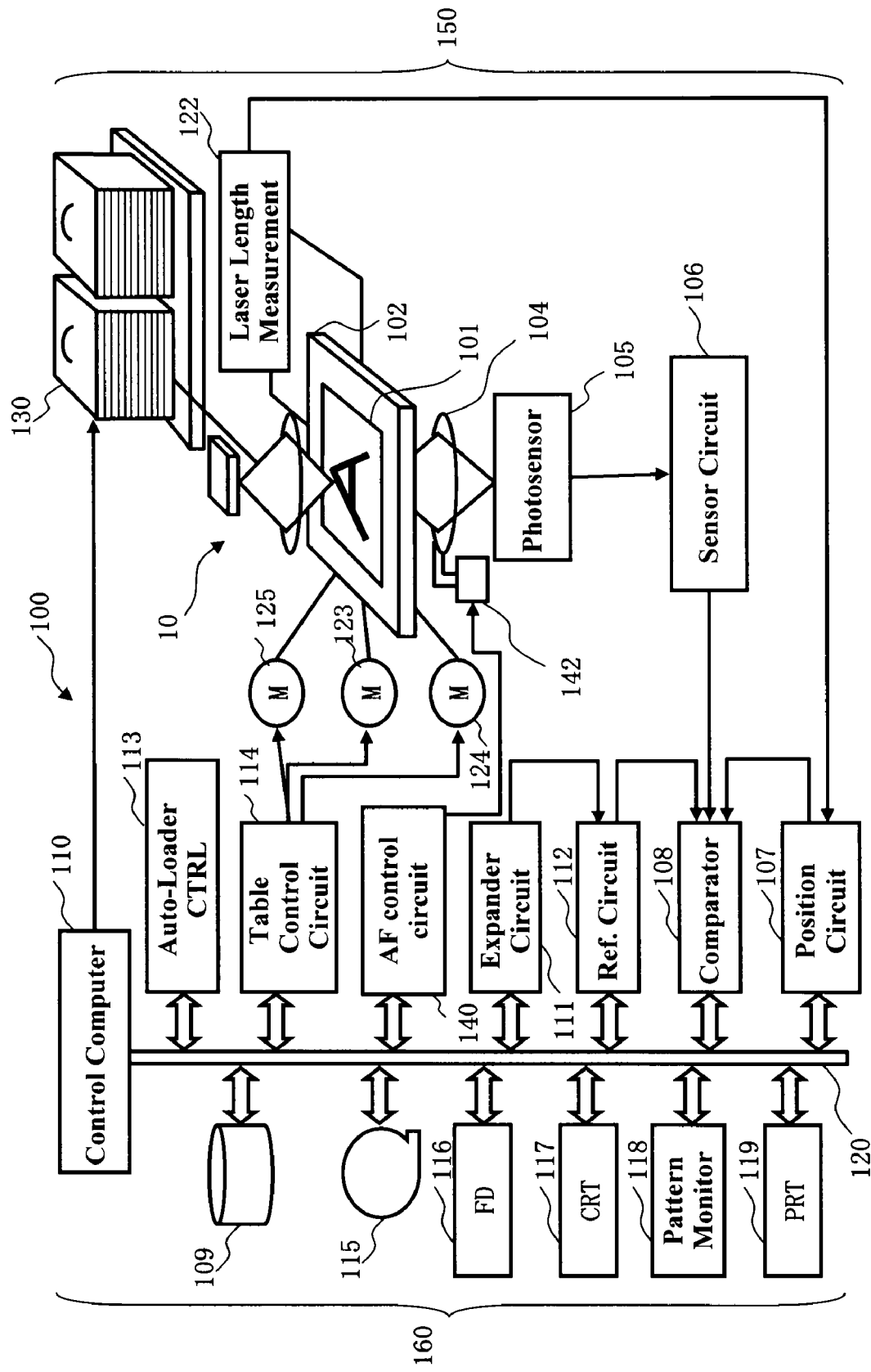
FIG. 6 depicts, in block diagram form, an overall configuration of a pattern inspection apparatus using the illumination apparatus embodying the invention.

FIG. 6 depicts, in block diagram form, an internal configuration of a workpiece pattern inspection system 100 using the illumination apparatus embodying the invention. The illustrative pattern inspection system 100 is for inspecting pattern defects of a workpiece 101 being tested, such as a substrate, e.g., a photomask, reticle, wafer or else. As shown herein, pattern inspection system 100 includes an optical image acquisition unit 150 and system control circuitry 160 associated therewith. The optical image acquisition unit 150 includes the illumination apparatus 10 shown in FIG. 1A for emission of deep UV illumination light 13. This unit 150 also includes a three-axis (X-Y-θ) driven table structure 102 for use as a workpiece support stage, image-magnifying optical system 104, photosensor unit 105 having an image-sensing photodiode array or else, sensor circuit 106, laser-based length measurement module 122, automatic workpiece loader 130, and piezoelectric element 142. The system controller 160 includes a digital computer machine 110 for system control, which is operatively connected via a bundle of data transfer buses 120 to a position circuit 107, comparator circuit 108, expander circuit 111, reference circuit 112, autofocus (AF) control circuit 140, auto-loader control circuit 113, table control circuit 114, magnetic disk device 109, magnetic tape device 115, floppy diskette drive (FDD) unit 116, cathode ray tube (CRT) display 117, pattern monitor 118, and printer 119. The X-Y-θ table 102 is driven by three separate electric motors, i.e., X-axis motor 123, Y-axis motor 124 and θ-axis motor 125. Pattern inspection system 100 may include other known functional modules needed for execution of pattern inspection operations, which are not specifically shown in FIG. 6 for brevity purposes only.

An operation of the pattern inspection system 100 is as follows. Firstly, a target object 101 is placed on the XYθ table 102. The object 101 may be a workpiece being tested, such as a photolithography mask having a top surface on which is formed or "printed" a ULSI circuit pattern containing therein a great number of figures indicated by ULSI design data. When pattern inspection system 100 is set in an optical image acquisition mode, the image acquisition unit 150 is rendered operative to acquire an optical image of the ULSI circuit pattern of photomask 101. This optical image acquisition will be performed in a way described below.

The test workpiece 101 is stably situated on the XYθ table 102, which is driven by respective motors 123-125 to move in X- and Y-axis directions on the horizontal plane and/or to rotate around Z axis by an angle θ. Then, the illumination apparatus 10 that overlies XYθ table 102 is activated to emit deep UV light for illumination of the surface of workpiece 101 having its circuit pattern being formed thereon. Light rays leaving illumination apparatus 10 fall onto test workpiece 101. The light that passed through workpiece 101 travels via the magnification optics 104 which is placed below XYθ table 102 and then reaches the photosensor unit 105 so that the pattern image is focused on its photosensitive surface. In this process, focus adjustment of the pattern image on test workpiece 101 is performed by using the piezoelectric element 142, which is under control of AF control circuit 140, to thereby absorb any possible warp of workpiece 101 and/or fluctuation of table 102 in Z axis.

Figure 7:
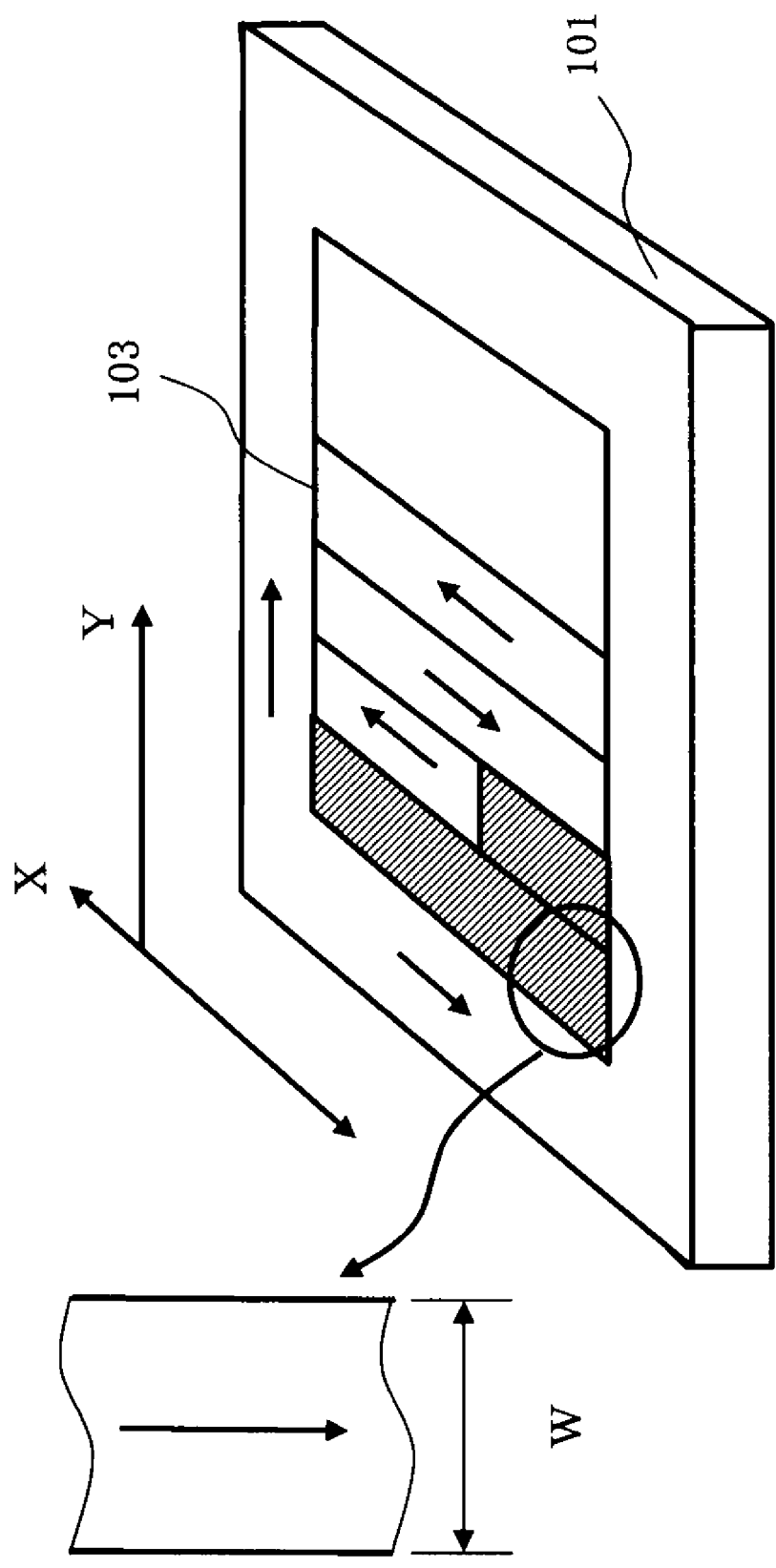
FIG. 7 is a perspective view of a target workpiece under pattern inspection, which is in the process of acquiring an optical image thereof.

As shown in FIG. 7, the test workpiece 101 has a circuit pattern area on its top surface, which area is virtually divided along Y direction into a group of parallel strip-like regions 103, each of which extends along X direction and has a scan width W. While the incident beam of illumination light 13 is falling onto workpiece 101, XYθ table 102 is driven to move in X and Y directions alternately under control of table controller 114 to thereby permit a beam spot on the workpiece surface to trace the workpiece area in a serpentine manner so that the strips 103 are scanned continuously. By such repeated forward and backward beam scanning operations in X direction, optical image segments with scan width W of the circuit pattern are sequentially sensed by photosensor unit 105, resulting in capture of a pattern image. More specifically, a first strip 103 of the test workpiece 101 is subjected to beam scanning in X direction, thereby to capture its optical image. Then, XYθ table 102 is driven to move in Y direction so that the beam hits a second strip 103 adjacent to the first strip. Next, table 102 is driven to move in the reverse direction along X axis for performing the scanning of second strip 103, resulting in capture of its optical image. Subsequently, table 102 is driven to shift in Y direction so that the beam spot rides on a third strip 103 next to the second strip. Then, table 102 is driven to move in the forward direction along X axis to thereby scan it in the same way as that during scanning of the first strip, resulting in capture of its optical image. This alternate forward/backward beam scanning in X direction will be repeated until an entire image of the test area of workpiece 101 is acquired. With such the "serpentine" scanning technique, strip images in the test area of workpiece 101 are continuously captured while reducing or minimizing the processing time required therefor.

The finally captured pattern image focused on the photosensor unit 105 is photoelectrically converted into an electrical image signal, which is then supplied to the sensor circuit 106 for analog-to-digital conversion (ADC) to a digital image signal. Photosensor 105 is designed to have a photodiode array or may be a time-delay integrator (TDI) sensor. By forcing XYθ table 102 to move continuously in opposite directions along X axis, TDI sensor captures an optical image of the pattern on test workpiece 101. Using the illumination apparatus 10 for emission of deep UV illumination light 13 along with the magnifier optics 104, photosensor 105 and sensor circuit 106 in the optical image acquisition unit 150 is devoted to achievement of a high-powered optical system suitable for pattern inspection.

The XYθ table 102 is driven by three-axis motors 123-125 under control of the table controller circuit 114 to move in X or Y direction or rotate about Z axis by an angle θ. These motors 123-125 may typically be stepper motors. A present coordinate position of XYθ table 102 moved is measured by the laser length measurement equipment 122, which supplies a position measurement signal to the position circuit 107. The test workpiece 101, such as a photomask, is loaded from auto-loader 130 and placed on table 102 in an automated way. After completion of pattern inspection, workpiece 101 is automatically unloaded therefrom by auto-loader 130.

The sensor circuit 106 generates at its output a measurement data signal indicative of the optical pattern image captured, which is sent forth to the comparator circuit 108 along with output data of position circuit 107 indicating the position of the test workpiece 101 on XYθ table 102. An example of the measured pattern data is eight-bit digital data with no signs added thereto, which represents brightness and gray-scale levels of respective picture elements or "pixels" of the image gained.

The ULSI circuit design data that was used for pattern formation or "print" on the test workpiece 101 is stored in the magnetic disk device 109, which is one example of a storage or "memory" device. This graphics design data is readable from magnetic disk device 109 via control computer 110 to expander circuit 111. Expander circuit 111 performs design data expansion processing in a way which follows. This circuit converts the readout design data of test workpiece 101 into two-value or multi-value image data, which is passed to the reference circuit 112. This circuit applies adequate filtering processing to the image data as sent thereto. Thus, it can be said that the optical pattern image data as obtained from sensor circuit 106 is in the state that the filtering was applied in conformity with image resolution characteristics of magnifier optics 104 and aperture effects of photosensor 105. In this state, there is a difference in characteristics between the design data-oriented "native" pattern image and the actually measured pattern image; so, the filtering is also applied to the design image data per se, thereby causing it to match or "tune" with the measured pattern data. In this way, a reference pattern image is created, which is used for comparison with the optical image.

The comparator circuit 108 performs an image comparison operation in a way which follows. Upon receipt of both the actually measured optical pattern image of the test workpiece 101 as supplied from the sensor circuit 106 based on the transmission image obtained from workpiece 101 and the reference image that was created by expander circuit 111 and reference circuit 112 for use as a reference image for pattern inspection, comparator 108 compares these images in accordance with a predetermined algorithm(s) to thereby determine whether defects are present in the measured pattern image of workpiece 101 being tested. With such the arrangement, it is possible to achieve a pattern inspection method of high reliability by use of the deep UV illumination light that is high in use efficiency.

It should be noted that the hardware components used in the illustrative embodiments may be implemented by computer-executable software programs or firmware modules or any possible combinations of hardware, software and firmware components. In case software programs are used, these are stored in a magnetic disk drive, magnetic tape recorder, FDD, read-only memory (ROM) device or electrically erasable programmable read-only memory (EEPROM) device, such as "Flash" memory. An example is that the table controller 114, expander circuit 111, reference circuit 112 and comparator circuit 108 making up the arithmetic control unit of pattern inspection system 100, these may be implemented by use of software programs executable by the system control computer 110 or, alternatively, by a combination of software programs and electrical circuits.

Although the invention has been disclosed and illustrated with reference to particular embodiments, the principles involved are susceptible for use in numerous other embodiments which will be apparent to persons skilled in the art. Similar beam scanning for workpiece pattern image acquisition is achievable by modifying the XYθ table 102 to stay at a fixed position while at the same time designing its associated optics to move relatively. Various modifications and changes in form and details may be made by those skilled in the art to which the invention pertains. The invention is, therefore, to be limited only as indicated by the scope of the appended claims, with its equivalents being involved therein.

What is claimed is:

1. An illumination apparatus comprising:
   a light source operative to yield a fundamental wave;
   a beam-shaping unit operative to perform beam shaping of the fundamental wave so that this wave has a prespecified shape;
   a pattern generator unit responsive to receipt of the beam-shaped fundamental wave, for converting the fundamental wave into illumination light shorter in wavelength than the fundamental wave to thereby produce illumination light of a predetermined shape; and
   an image relay unit operative to guide the illumination light produced by said pattern generator unit to fall onto a target object.

2. The apparatus according to claim 1, wherein said fundamental wave is coherent light and wherein said illumination light is coherent light with a wavelength of 266 nanometers (nm) or less.

3. The apparatus according to claim 1, wherein said pattern generator unit is an area light emitter having a surface for emitting illumination light with a prespecified shape.

4. The apparatus according to claim 1, wherein said pattern generator unit has a surface made of particles of a nonlinear material for emitting illumination light having a prespecified shape.

5. The apparatus according to claim 1, wherein said pattern generator unit has a surface made of a porous nonlinear material for emitting illumination light having a prespecified shape.

6. A pattern inspection apparatus for inspecting a pattern of an object being tested, said apparatus comprising:
   a light source for emission of a fundamental wave;
   a beam-shaping unit for shaping the fundamental wave to provide a wave having a prespecified shape;
   a pattern generator unit responsive to receipt of the beam-shaped fundamental wave for converting this fundamental wave into illumination light with a wavelength of 266 nm or less and for generating the illumination light having a predetermined shape;
   an image relay unit for guiding the illumination light generated by said pattern generator unit to fall onto the object; and
   a light-receiving unit for receiving light indicative of the pattern of said object.

7. A beam irradiation apparatus adaptable for use in a lithographic pattern inspection system for checking a workpiece for pattern defects, said apparatus comprising:
   a light source operative to yield coherent light with a first wavelength;
   a beam-shaping unit optically coupled to the light source for receiving the light and for applying thereto beam-shaping to thereby produce a beam-shaped light beam;
   a pattern generator optically coupled directly to the beam-shaping unit for applying wavelength conversion to the beam-shaped light beam to thereby generate a beam of light for use as illumination light having a second wavelength less than the first wavelength; and
   an optical image relay optically coupled at its one end to said pattern generator for causing the illumination light to output at a remaining end thereof and fall onto the workpiece in the pattern inspection system while retaining an image indicated by the light being transmitted through said optical image relay.

8. The apparatus of claim 7 wherein said light source includes:
   a laser device for emission of a beam of deep ultraviolet (UV) light;
   a Q-switch modulator coupled to the laser oscillator; and
   a laser amplifier coupled to the Q switch.

9. The apparatus of claim 8 wherein said laser device includes a neodymium (Nd)-doped yttrium-aluminum-garnet (YAG) laser oscillator for emitting by third harmonic generation (THG) a beam of third harmonic wave light with a wavelength of about 355 nanometers (nm).

10. The apparatus of claim 7 wherein said light source includes:
   a pair of laser oscillators for emitting fundamental waves different in wavelength from each other;
   a harmonic wave generator optically coupled to one of the laser oscillators for generating a frequency-converted fundamental wave; and
   a sum frequency wave generator having a first input coupled to a remaining one of the laser oscillators and a second input coupled to said harmonic wave generator, for producing a wave having its frequency equivalent to a sum of frequencies of coaxially incoming fundamental waves.

11. The apparatus of claim 10 wherein said sum frequency wave generator comprises a nonlinear crystal body.

12. The apparatus of claim 7 wherein the first wavelength is set to approximately 355 nm whereas the second wavelength is set at about 266 nm or less.

13. The apparatus of claim 7 wherein said pattern generator is of a surface emission type in structure.

14. The apparatus of claim 13 wherein said pattern generator comprises:
   a pair of spaced-apart optical transparent plates made of quartz glass;
   a fine-particle nonlinear crystal layer interposed between the plates; and
   a heat release member supporting thereon said plates with the nonlinear crystal layer sandwiched therebetween.

15. The apparatus of claim 14 wherein the nonlinear crystal layer is made of fine particles of a cesium triborate (CBO) crystal.

16. The apparatus of claim 15 wherein the particles of CBO crystal have a diameter of less than or equal to 100 micrometers ($\mu$m).

17. The apparatus of claim 16 wherein the diameter is preferably set to range from 10 $\mu$m to 0.1 $\mu$m.

18. The apparatus of claim 13 wherein said pattern generator comprises:
   a substrate; and
   a nonlinear crystal powder layer on the substrate.

19. The apparatus of claim 18 wherein the nonlinear crystal powder layer is made of CBO crystal particles.

20. The apparatus of claim 13 wherein said pattern generator comprises:
   a couple of spaced-apart quartz glass plates; and
   a nonlinear crystal powder layer sandwiched therebetween.

* * * * *